(12) United States Patent
Suzuki et al.

(10) Patent No.: US 9,727,969 B2
(45) Date of Patent: Aug. 8, 2017

(54) IMAGE PROCESSING DEVICE, IMAGE PROCESSING METHOD, PROGRAM, AND IMAGE PROCESSING SYSTEM

(71) Applicant: Sony Corporation, Tokyo (JP)

(72) Inventors: Masaru Suzuki, Tokyo (JP); Shinichiro Gomi, Tokyo (JP)

(73) Assignee: Sony Corporation (JP)

( * ) Notice: Subject to any disclaimer, the term of this patent is extended or adjusted under 35 U.S.C. 154(b) by 97 days.

(21) Appl. No.: 14/420,505

(22) PCT Filed: Jul. 2, 2013

(86) PCT No.: PCT/JP2013/068141
§ 371 (c)(1),
(2) Date: Feb. 9, 2015

(87) PCT Pub. No.: WO2014/027523
PCT Pub. Date: Feb. 20, 2014

(65) Prior Publication Data
US 2015/0199819 A1     Jul. 16, 2015

(30) Foreign Application Priority Data
Aug. 17, 2012    (JP) ................. 2012-180860

(51) Int. Cl.
*G06T 7/00*     (2017.01)
*A61B 5/00*     (2006.01)
*A61B 5/103*    (2006.01)
*G06T 7/90*     (2017.01)
(Continued)

(52) U.S. Cl.
CPC .......... *G06T 7/0081* (2013.01); *A61B 5/0037* (2013.01); *A61B 5/1032* (2013.01);
(Continued)

(58) Field of Classification Search
CPC ..... A61B 5/0037; A61B 5/1032; A61B 5/444; G06T 7/408; G06T 2207/10024;
(Continued)

(56) References Cited

U.S. PATENT DOCUMENTS 6,674,431 B1 *   1/2004   Enomoto .............. G06T 7/0024
                                         345/419
2004/0028263 A1   2/2004   Sakamoto
(Continued)

FOREIGN PATENT DOCUMENTS

JP        11-326057 A     11/1999
JP        2004-041753 A   2/2004
(Continued)

OTHER PUBLICATIONS

International Search Report from International Publication No. PCT/JP2013/068141 mailed Aug. 6, 2013.

*Primary Examiner* — Yon Couso
(74) *Attorney, Agent, or Firm* — Lerner, David, Littenberg, Krumholz & Mentlik, LLP

(57) ABSTRACT

Provided is an image processing device including a dividing unit which divides a captured image of skin into regions in a multidimensional manner, a feature value calculating unit which calculates a feature value of a color property in each region divided by the dividing unit, and an evaluating unit which calculates an evaluation value of the skin using the feature values calculated by the feature value calculating unit.

1 Claim, 19 Drawing Sheets

(51) Int. Cl.
*G06K 9/00* (2006.01)
*G06K 9/46* (2006.01)

(52) U.S. Cl.
CPC ............... *A61B 5/444* (2013.01); *G06T 7/90* (2017.01); *G06K 9/00281* (2013.01); *G06K 9/4652* (2013.01); *G06T 2207/10024* (2013.01); *G06T 2207/20076* (2013.01); *G06T 2207/30088* (2013.01); *G06T 2207/30196* (2013.01); *G06T 2207/30201* (2013.01)

(58) Field of Classification Search
CPC . G06T 2207/30196; G06T 2207/20076; G06T 2207/30201; G06T 7/0081; G06T 2207/30088; G06T 7/90; G06K 9/00281; G06K 9/4652
USPC .......................................... 382/164
See application file for complete search history.

(56) References Cited

U.S. PATENT DOCUMENTS

| | | | | |
|---|---|---|---|---|
| 2007/0127787 | A1* | 6/2007 | Castleman | G06K 9/00248 382/118 |
| 2009/0245603 | A1* | 10/2009 | Koruga | A45D 44/00 382/128 |
| 2014/0378779 | A1* | 12/2014 | Freeman | A61B 5/0051 600/301 |
| 2015/0213619 | A1* | 7/2015 | Nakamura | A61B 5/0077 382/128 |

FOREIGN PATENT DOCUMENTS

| | | |
|---|---|---|
| JP | 2008-293325 A | 12/2008 |
| JP | 2010-179012 A | 8/2010 |
| JP | 2011-118671 A | 6/2011 |

* cited by examiner (A)   (B)

FEATURE VALUE CALCULATION REGION

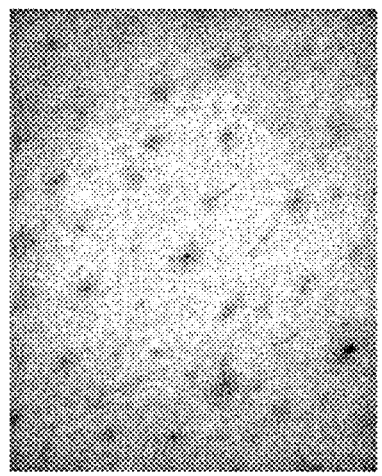
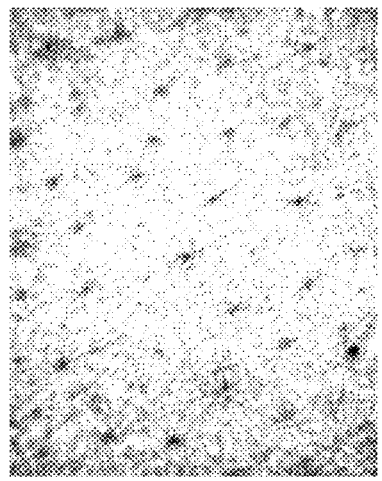
FIG. 17

IMAGE PROCESSING DEVICE, IMAGE PROCESSING METHOD, PROGRAM, AND IMAGE PROCESSING SYSTEM

CROSS-REFERENCE TO RELATED APPLICATION

The present application is a national phase entry under 35 U.S.C. §371 of International Application No. PCT/JP2013/068141 filed Jul. 2, 2013, published on Feb. 20, 2014 as WO 2014/027523 A1, which claims priority from Japanese Patent Application No. JP 2012-180860 filed in the Japanese Patent Office on Aug. 17, 2012.

TECHNICAL FIELD

The present technology enables skin color evaluation with good accuracy in an image processing device, an image processing method, a program, and an image processing system.

BACKGROUND ART

Heretofore, in skin counseling, the skin color of a user is measured, and then various pieces of advice based on the measurement results are given to the user. In the skin color measurement, Patent Literature 1, for example, sets the entire skin color portion of the face except trouble portions or shadow portions as a skin color measurement area, and then creates a histogram using an image of the skin color measurement area. Furthermore, by calculating an average value of n % pixels of all the pixels from a higher frequency color based on the histogram, the color is measured.

CITATION LIST

Patent Literature

Patent Literature 1: JP 2010-179012A

SUMMARY OF INVENTION

Technical Problem

When the entire skin color portion of the face except trouble portions or shadow portions is set as the skin color measurement area, there is a possibility that the histogram varies depending on body hair regions, pore regions, and spot regions in the area, and therefore the skin color cannot be evaluated with good accuracy.

Then, it is an object of the present technology to provide an image processing device, an image processing method, a program, and an image processing system capable evaluating skin color with good accuracy.

A first aspect of the present technology is an image processing device including a dividing unit which divides a captured image of skin into regions in a multidimensional manner, a feature value calculating unit which calculates a feature value of a color property in each region divided by the dividing unit, and an evaluating unit which calculates an evaluation value of the skin using the feature values calculated by the feature value calculating unit.

Solution to Problem

In the present technology, a dividing unit divides a captured skin image into regions in a multidimensional manner. For example, the skin image is divided into regions in the planar direction to be divided into a skin region and non-skin regions. Moreover, captured images at different positions in the depth direction generated while controlling a polarization plane of a light source and an imaging unit which generates the captured images are obtained, captured images at different positions in the depth direction generated while controlling the focal length of the imaging unit are obtained, or captured images at different positions in the depth direction based on an intensity distribution and traveling direction information of light are generated, and then the images are divided into a skin surface region and a region inside the skin. Furthermore, the non-skin regions are divided into at least any one of a pore region, a spot region, and a body hair region and the skin region is divided based on each skin component. A feature value calculating unit calculates a feature value of a color property in each of such divided regions. As the color property, at least any one of the brightness, color, and transparency of the skin is used. Thus, a skin evaluation value is calculated by an evaluating unit using the feature value calculated in each region. Moreover, the feature value is weighted in each region, and then the skin evaluation value is also calculated using the weighted feature values. The feature value and the evaluation value are calculated after performing exclusion processing of excluding greatly different values.

A second aspect of the present technology is an image processing method including a step of dividing a captured image of skin into regions in a multidimensional manner, a step of calculating a feature value of a color property in each divided region, and a step of calculating an evaluation value of the skin using the calculated feature values.

A third aspect of the present technology is a program which causes a computer to execute skin evaluation. The program causes the computer to execute processing of dividing a captured image of skin into regions in a multidimensional manner, processing of calculating a feature value of a color property in each divided region, and processing of calculating an evaluation value of the skin using the calculated feature values.

In addition, a program according to the present technology is a program capable of being provided via a recording medium or a communication medium providing various programs and codes, for example, to a general purpose computer executable of the same in a computer-readable format, for example, a recording medium, such as an optical disk, a magnetic disk, and a semiconductor memory, or a communication medium, such as a network. Such a program realizes a computer performing processes according to the program, provided in a computer-readable format.

A fourth aspect of the present technology is an image processing system including an imaging device and an information processing device. The imaging device includes an imaging unit of generating a captured image of skin, and either the imaging device or the information processing device includes a dividing unit which divides the captured image of the skin into regions in a multidimensional manner, a feature value calculating unit which calculates a feature value of a color property in each region divided by the dividing unit, an evaluating unit which calculates an evaluation value of the skin using the feature values calculated by the feature value calculating unit, and a presentation unit which presents an evaluation result based on the evaluation value of the skin.

Advantageous Effects of Invention

According to the present technology, a skin image is divided into regions in a multidimensional manner, a feature value of a color property is calculated in each divided region, and then a skin evaluation value is calculated using the calculated feature values. Therefore, the skin color can be evaluated with good accuracy as compared with the case where the skin color is evaluated in the entire skin image without performing the region division. The effects described in this specification are merely examples and are not limited, and additional effects may be demonstrated.

BRIEF DESCRIPTION OF DRAWINGS

FIG. 17 includes FIGS. 17(A) and 17(B) which are views illustrating a skin image.

DESCRIPTION OF EMBODIMENTS

Hereinafter, embodiments for carrying out the present technology are described. The description is given in the following order:
1. Image Processing System
2. First Embodiment
2-1. Configuration of First Embodiment
2-2. Operation of First Embodiment
3. Second Embodiment
3-1. Configuration of Second Embodiment
3-2. Operation of Second Embodiment
4. Third Embodiment
4-1. Configuration of Third Embodiment
4-2. Operation of Third Embodiment
5. Fourth Embodiment
5-1. Configuration of Fourth Embodiment
5-2. Operation of Fourth Embodiment.

1. Image Processing System

Figure 1:
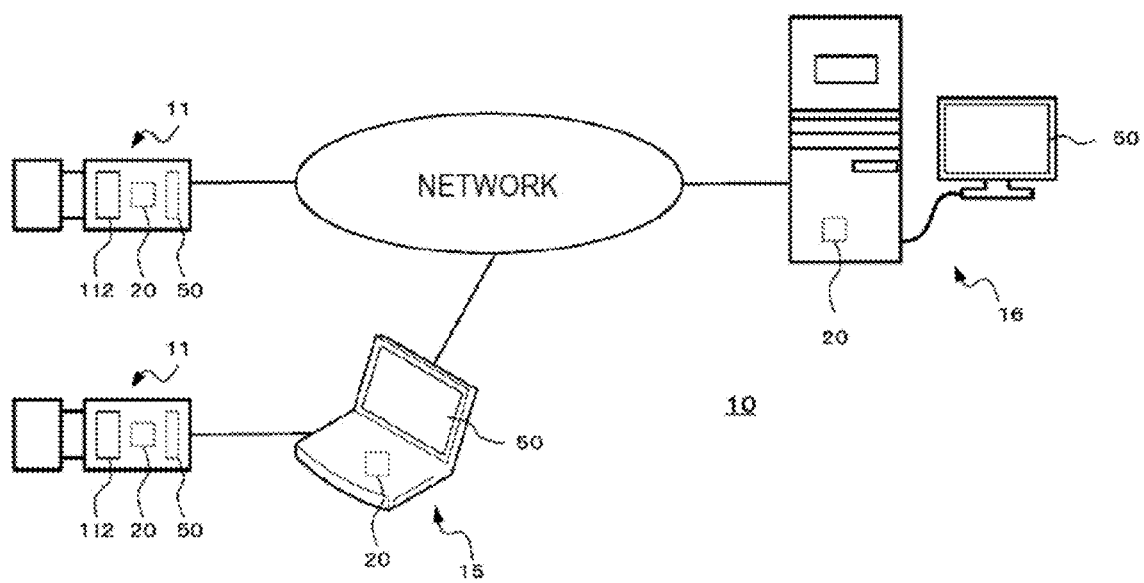
FIG. 1 is a view illustrating the configuration of an image processing system.

FIG. 1 illustrates the configuration of an image processing system of the present technology. An image processing system 10 is constituted using a device having an imaging function (hereinafter referred to as an "imaging device") 11, information processing devices 15 and 16, and the like. The imaging device 11 and the information processing device (for example, a personal computer device and the like) 15 can be directly connected through a wired or wireless transmission path. The imaging device 11 and the information processing device (for example, a server device and the like) 16 can be connected through a network and the like of a public telecommunication network.

The imaging device 11 has an imaging unit 112 which generates a captured skin image. Any one of the imaging device 11 or the information processing devices 15 and 16 is provided with an image processing device 20 which evaluates skin. The image processing device 20 has a dividing unit which divides a captured skin image (hereinafter referred to as "a skin image") into regions in a multidimensional manner. The image processing device 20 also has a feature value calculating unit which calculates a feature value of a color property in each region divided by the dividing unit and an evaluating unit which calculates a skin evaluation value using the feature values calculated by the feature value calculating unit. Furthermore, any one of the imaging device 11 or the information processing devices 15 and 16 is provided with a presentation unit 50 which presents the evaluation result based on the skin evaluation value. A skin image for use in the skin evaluation by the image processing device 20 is not limited to a skin image output from the imaging unit 112 and may be a skin image generated by the imaging unit 112 and stored in a recording medium and the like.

2. First Embodiment

A first embodiment describes a case where a skin image is divided into regions in the planar direction, and then evaluates the divided skin regions.

Figure 2:
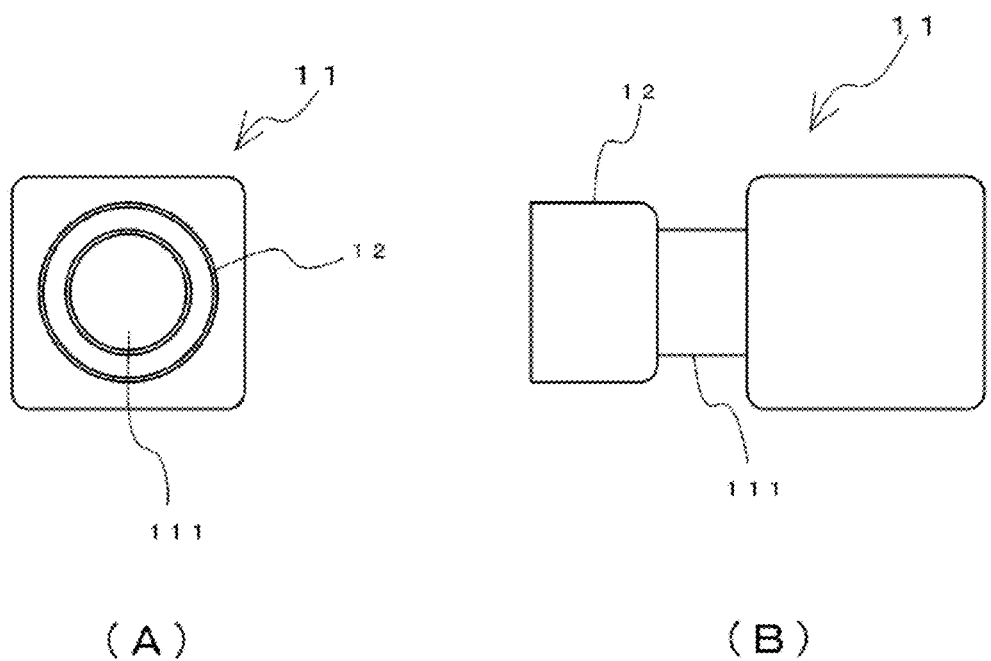
FIG. 2 includes FIGS. 2(A) and 2(B) which are views illustrating the configuration of an imaging device in a simplified manner.
Figure 3:
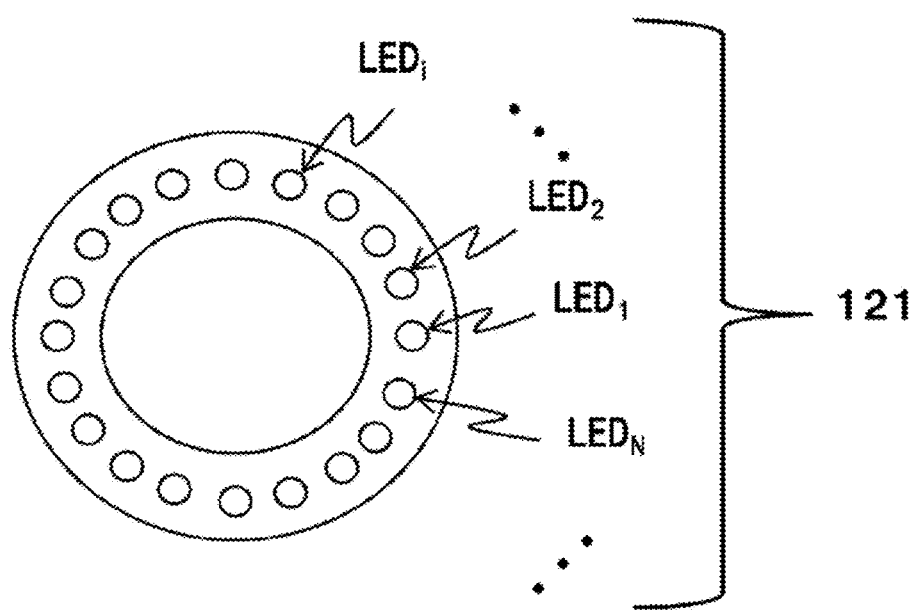
FIG. 3 is a view illustrating a light source as an attachment.
Figure 4:
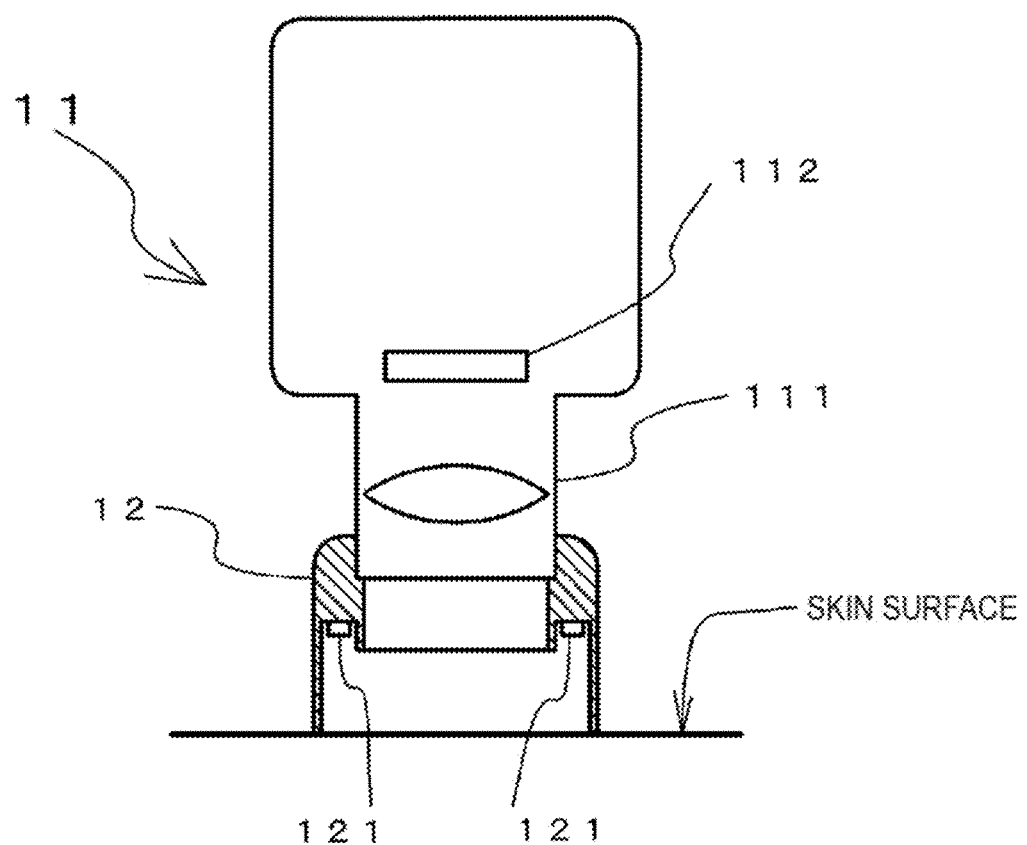
FIG. 4 is a view illustrating the position of the imaging device in imaging.

FIG. 2 illustrates the configuration of an imaging device which images skin in a simplified manner. FIG. 2(A) is a front view of the imaging device 11 and FIG. 2(B) is a side view of the imaging device 11. An attachment 12 is provided on the top end of a camera cone 111 of the imaging device 11. The attachment 12 may be integrally constituted with the camera cone 111 or may be detachable to/from the camera cone 111. On the attachment 12, a plurality of light sources 121 (for example, LED1 (light emitting diode) to LEDn) constituting a lighting unit are disposed in a ring shape as illustrated in FIG. 3. As the light source, a white LED is suitable. As illustrated in FIG. 4, for example, the imaging device 11 provided with the attachment 12 is closely attached to the skin surface, and then captures a skin image. For lighting the skin, not only the attachment 12 but other lighting devices may be used.

[2-1. Configuration of First Embodiment]

Figure 5:
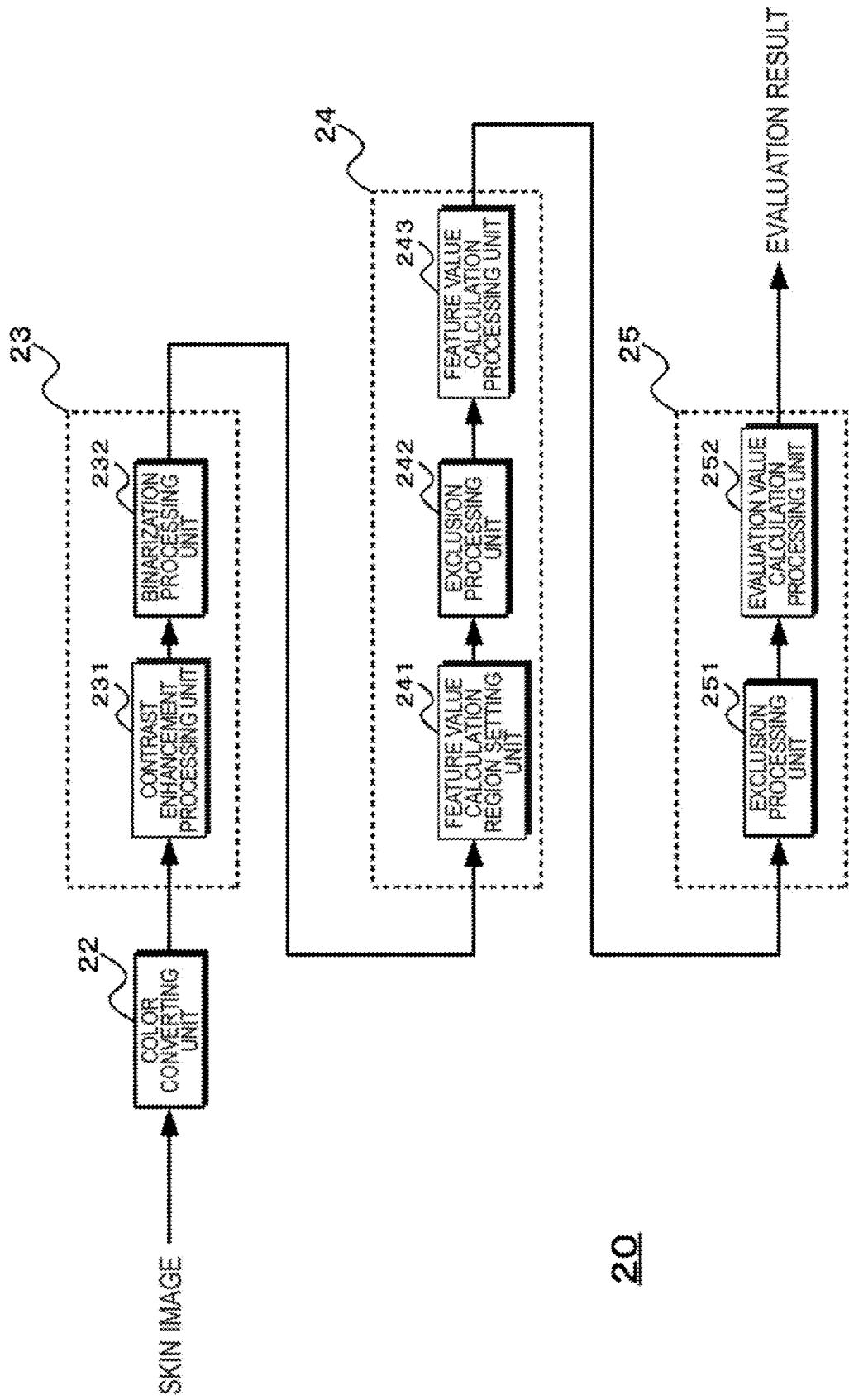
FIG. 5 is a view illustrating the configuration of a first embodiment of an image processing device.

FIG. 5 illustrates the configuration of the first embodiment of the image processing device. An image processing device 20 has a color converting unit 22, a region dividing unit 23, a feature value calculating unit 24, and an evaluating unit 25. The region dividing unit 23 has a contrast enhancement processing unit 231 and a binarization processing unit 232. The feature value calculating unit 24 has a feature value calculation region setting unit 241, an exclusion processing unit 242, and a feature value calculation processing unit 243. The evaluating unit 25 has an exclusion processing unit 251 and an evaluation value calculation processing unit 252.

The color converting unit 22 converts a color space of the skin image into a desired color space. The color converting unit 22 converts the skin space to a desired color space, for example, an HSV color space which is a color space suitable for skin evaluation. The color converting unit 22 may convert the color space to a L*a*b* color space. In the HSV color space, the H value corresponds to the skin hue, the S value corresponds to the skin saturation, and the V value corresponds to the skin brightness. In the L*a*b* color space, the L* value corresponds to the skin brightness and tan-1 (b*/a*) corresponds to the skin hue.

The contrast enhancement processing unit 231 of the region dividing unit 23 performs contrast enhancement processing to thereby enable appropriate binarization processing. The contrast enhancement processing unit 231 performs contrast enhancement processing, e.g., processing based on a histogram, such as contrast limited adaptive histogram equalization (CLAHE), of the S values of the HSV color space to generate a contrast enhanced image. The contrast enhancement processing unit 231 may perform a gamma correction process of the S values to generate an image in which the contrast is enhanced. The contrast enhancement processing unit 231 may perform contrast enhancement processing of the L* values of the L*a*b* color space to generate a contrast enhanced image.

The binarization processing unit 232 compares the contrast enhanced image generated by the contrast enhancement processing unit 231 and a predetermined threshold value to generate a binarized image in which the skin image is binarized to a skin region and non-skin regions.

The feature value calculation region setting unit 241 of the feature value calculating unit 24 sets a plurality of feature value calculation regions in the skin region. The feature value calculation region setting unit 241 sets a plurality of feature value calculation regions of a polygonal shape, a circular shape, an oval shape, and the like in the skin region. The feature value calculation regions may be different in the shape or size and may have a portion where a region is overlapped with another region.

The exclusion processing unit 242 excludes greatly different values in the H values and the V values of the HSV color space in each feature value calculation region. The exclusion processing unit 242 performs, for example, a test of rejection of the H values and the V values in each feature value calculation region, and then excludes greatly different values. As the test of rejection, a test of rejection, such as a test of rejection of Smirnoff-Grubbs, a test of rejection of Masuyama, and a test of rejection of Thompson, and the like can be used.

The feature value calculation processing unit 243 performs statistical processing using the H values and the V values after the exclusion processing of the HSV color space in each feature value calculation region, and then calculates the feature value of the color property. The feature value calculation processing unit 243 calculates an average value by the statistical processing to give the same as the feature value. As the feature value, the mode, the median value, and the maximum value may be used. When the number of the H values and the V values which represent that reflection is strongly saturated increases, the minimum value may be used.

Thus, the feature value calculation processing unit 243 calculates the feature value using the H values and the V values after the exclusion processing of the HSV color space, and therefore can calculate the feature value which strongly reflects the feature of the feature value calculation region as compared with the case where the feature value is calculated using the H values and the V values which are not subjected to the exclusion processing.

The exclusion processing unit 251 of the evaluating unit 25 performs processing of excluding a feature value whose value is greatly different from that of the feature value calculated in each feature value calculation region. The exclusion processing unit 251 performs a test of rejection of the feature value calculated in each feature value calculation region using the H values and a test of rejection of the feature value calculated in each feature value calculation region using the V values, and then excludes a feature value whose value is greatly different. As the test of rejection, a test of rejection, such as a test of rejection of Smirnoff-Grubbs, a test of rejection of Masuyama, and a test of rejection of Thompson, and the like can be used as described above.

The evaluation value calculation processing unit 252 performs statistical processing using the feature value after the exclusion processing to calculate an evaluation value of a color property. The evaluation value calculation processing unit 252 performs statistical processing using the feature value after the H values are subjected to the exclusion processing, and then calculates an average value, for example, to give the same as an evaluation value. As the evaluation value, the mode and the median value may be used. Similarly, the evaluation value calculation processing unit 252 performs statistical processing using the feature value after the V values are subjected to the exclusion processing, and then calculates an average value, for example, to give the same as an evaluation value. As the evaluation value, the mode and the median value may be used.

Thus, the evaluation value calculation processing unit 252 calculates the evaluation value from the feature values after the exclusion processing of the HSV color space, and therefore the evaluation value is a value which strongly reflects the feature of the skin region as compared with the case where the evaluation value is calculated from the feature values which are not subjected to the exclusion processing.

[2-2. Operation of First Embodiment]

Figure 6:
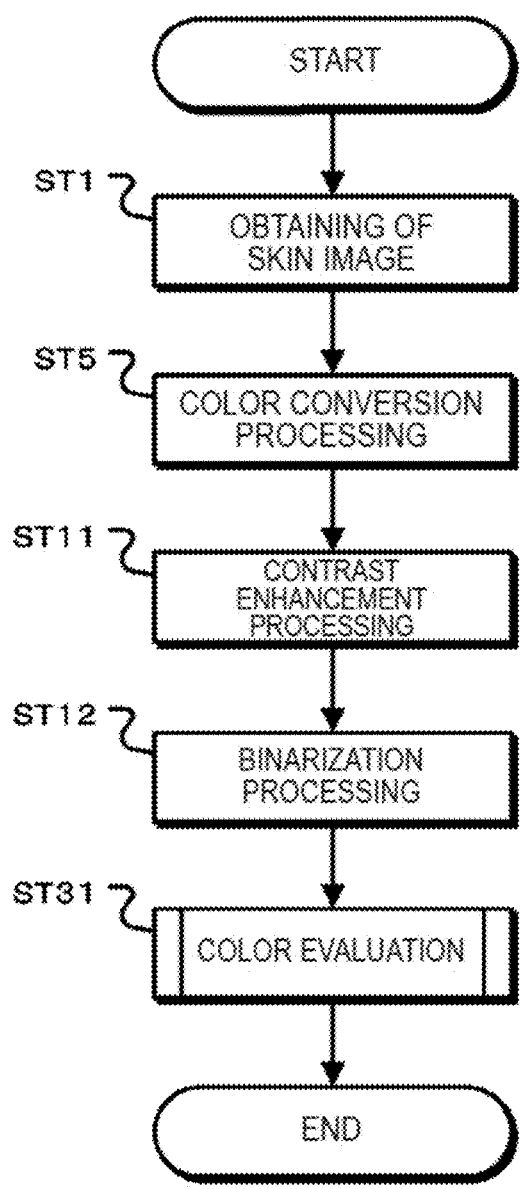
FIG. 6 is a flow chart showing an operation of the first embodiment of the image processing device.

FIG. 6 is a flow chart showing an operation of the first embodiment of the image processing device 1.

In Step ST1, the image processing device 20 obtains a skin image. The image processing device 20 obtains the skin image generated by the imaging device 11 or the skin image generated by the imaging device 11, and then stored. Then, the process proceeds to Step ST5.

In Step ST5, the image processing device 20 performs color conversion processing of the skin image. The image processing device 20 converts the skin image into an HSV color space (or L*a*b* color space), for example. Then, the progress proceeds to Step ST11.

In Step ST11, the image processing device 20 performs contrast enhancement processing. The image processing device 20 performs contrast enhancement processing of an image of the S values suitable for skin region division in such a manner that suitable binarization processing can be performed. Then, the process proceeds to Step ST12.

In Step ST12, the image processing device 20 performs binarization processing. The image processing device 20 performs binarization processing using an image subjected to the contrast enhancement processing, and then divides the skin image into a skin region and non-skin regions. Then, the process proceeds to Step ST31.

Figure 7:
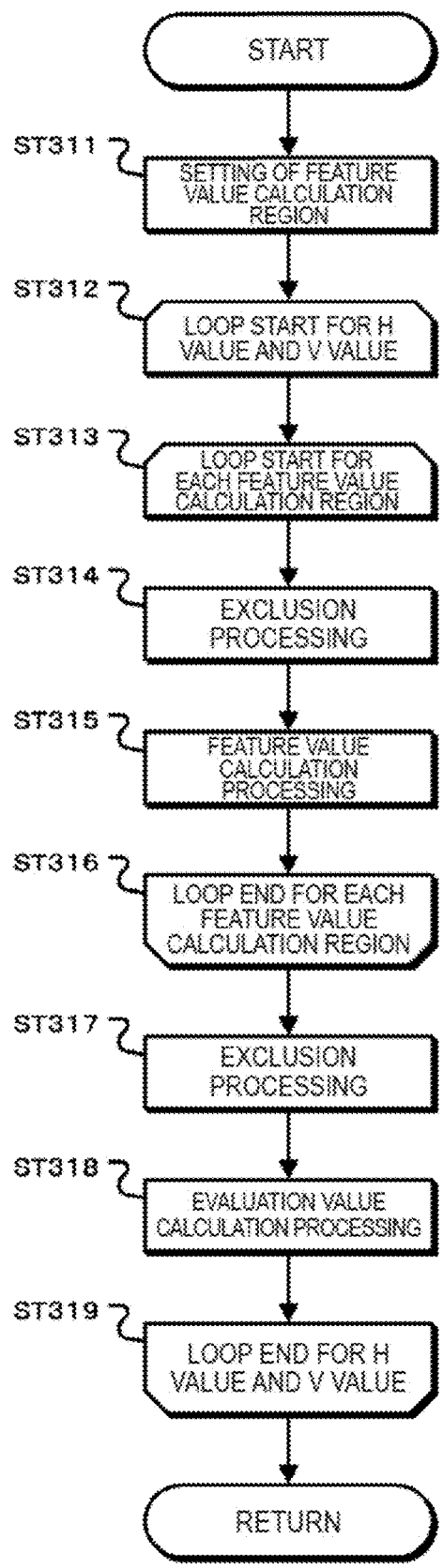
FIG. 7 is a flow chart showing color evaluation.

In Step ST31, the image processing device 20 performs color evaluation. FIG. 7 is a flow chart showing the color evaluation.

In Step ST311, the image processing device 20 sets the feature value calculation regions. The image processing device sets the feature value calculation regions in the skin region, for example. Then, the process proceeds to Step ST312.

Step ST312 is a loop start point for the H value and the V value and Step ST313 is a loop start point for each feature value calculation region.

In Step ST314, the image processing device 20 performs exclusion processing. The image processing device 20 excludes greatly different values in the feature value calculation regions. Then, the process proceeds to Step ST315.

In Step ST315, the image processing device 20 performs feature value calculation processing. The image processing device 20 performs statistical processing using the values after the exclusion processing in the feature value calculation regions, and then calculates the feature value of the color of each of the feature value calculation regions. Then, the process proceeds to Step ST316.

Step ST316 is a loop end point for each feature value calculation region. More specifically, the feature value is calculated in each feature value calculation region by the processing from Step ST313 to Step ST316.

In Step ST317, the image processing device 20 performs exclusion processing. The image processing device 20 excludes the feature value of greatly different values in the feature value calculated in each feature value calculation region. Then, the process proceeds to Step ST318.

In Step ST318, the image processing device 20 performs evaluation value calculation processing. The image processing device 20 performs statistical processing using the feature values after the exclusion processing, and then calculates the evaluation value of color. Then, the process proceeds to Step ST319.

In Step ST319, the image processing device 20 is a loop end point about an image of the H values and the V values. More specifically, the evaluation value is calculated about each of a group of the H values and a group the V values by the processing from Step ST311 to Step ST319.

Figure 8:
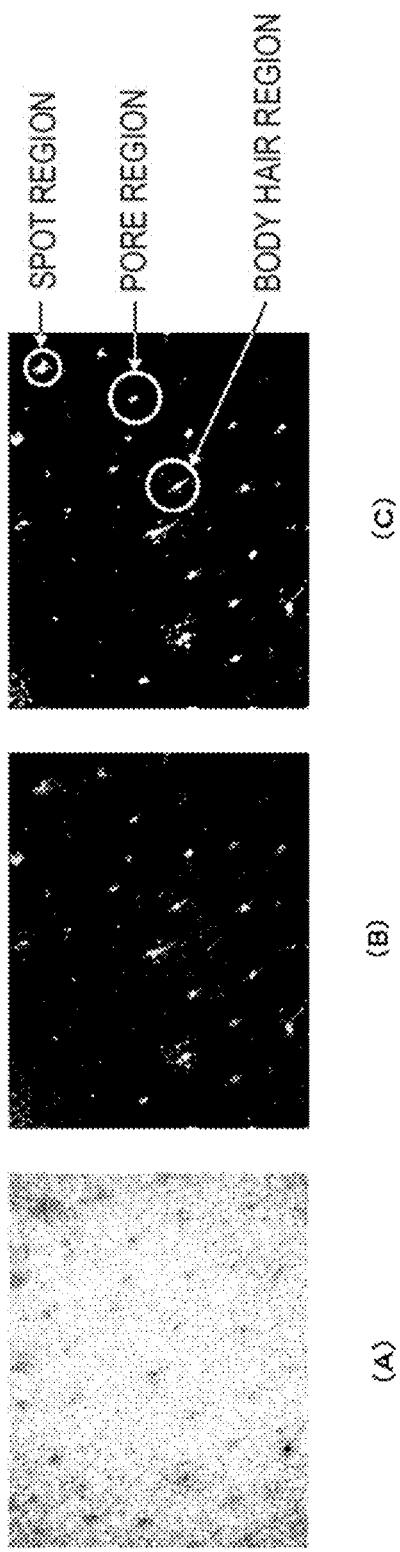
FIG. 8 includes FIGS. 8(A) to 8(C) which are views illustrating an operation to region division.

Next, an example of the operation of the image processing device 20 is described. FIG. 8 illustrates an example of operations up to region division. FIG. 8(A) illustrates a skin image (for example, an RGB image). When the skin image is converted to the HSV color space from the RGB color space, the image of the S values is an image illustrated in FIG. 8(B). When the image of the S values is subjected to the contrast enhancement processing, and then subjected to the binarization processing, a binarized image illustrated in FIG. 8(C), for example, is obtained. In the binarized image, white regions represent body hair regions, pore regions, spot regions, mole regions, and the like, and the remaining black region represents a skin region. Therefore, in order to obtain the evaluation result of only the skin region, the feature value calculation regions are set in the skin region.

Figure 9:
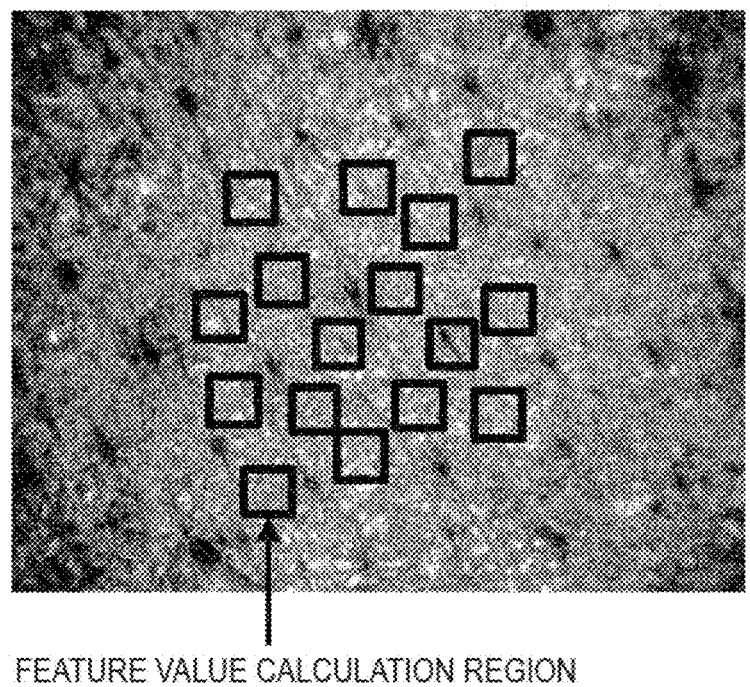
FIG. 9 is a view illustrating the set state of feature value calculation regions.

FIG. 9 illustrates a set state of the feature value calculation regions. FIG. 9 illustrates an example of the case where a plurality of rectangular feature value calculation regions are provided on the skin image.

Thus, by setting the feature value calculation regions in the skin region, performing the exclusion processing of the H values and the V values of the feature value calculation regions, and then calculating the feature value, the feature value which strongly reflects the feature of the feature value calculation regions can be calculated. Furthermore, by calculating an evaluation value after performing the exclusion processing of the feature value in each feature value calculation region, an evaluation value which strongly reflects the feature of the skin region can be calculated.

Figure 10:
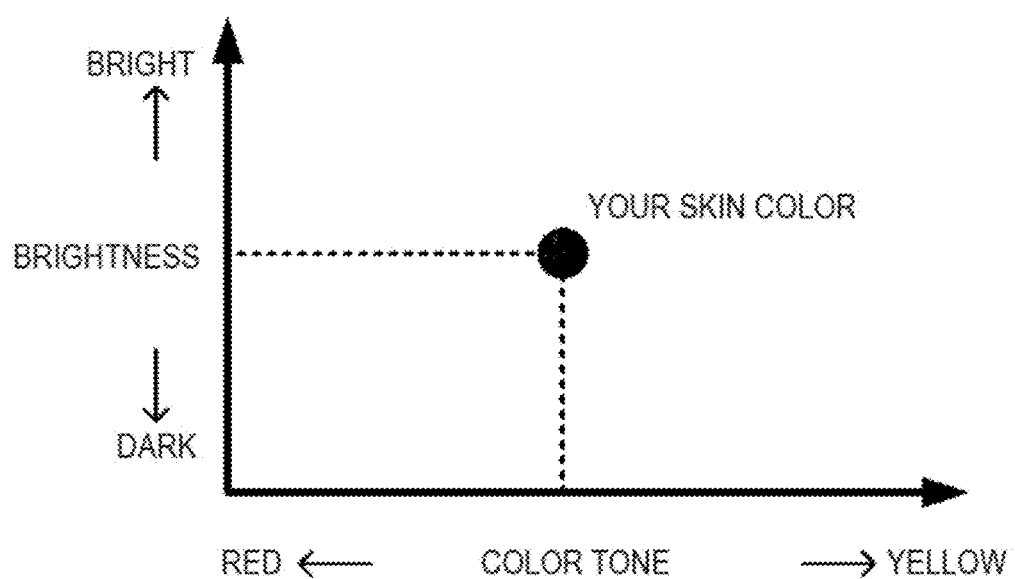
FIG. 10 is a view illustrating a case where the evaluation results are graphed as an example.

Thus, based on the calculated evaluation value, the skin evaluation result is shown by the presentation unit 50. In the presentation of the evaluation result, the evaluation value may be output with numerical values or the evaluation value may be output by graphical representation. FIG. 10 illustrates the case where the evaluation result is shown by graphical representation as an example. For example, the horizontal axis of the graph is set as the coordinate axis of the evaluation value (evaluation values based on the H values) which represent the skin color tone and the vertical axis is set as the coordinate axis of the evaluation values (evaluation values based on the V values) which represent the skin brightness. Then, the coordinate position based on the calculated evaluation values is represented as the evaluation position of a user's skin.

As described above, in the first embodiment, the skin region is divided from the skin image, and then the feature value of the color property is calculated in the skin region. Furthermore, the calculated feature values are used as the skin evaluation values. Therefore, the color of the skin region can be evaluated with good accuracy as compared with the case where the evaluation value is calculated from the entire skin image without performing the skin region division. Moreover, in the first embodiment, the exclusion processing of excluding greatly different values is performed, and then the evaluation value is calculated, and therefore the evaluation value which strongly reflects the feature of the region can be calculated.

3. Second Embodiment

Next, a second embodiment describes a case where a skin image is divided into regions in the planar direction, the evaluation results of the divided skin region and the non-skin regions are integrated to evaluate the skin.

[3-1. Configuration of Second Embodiment]

Figure 11:
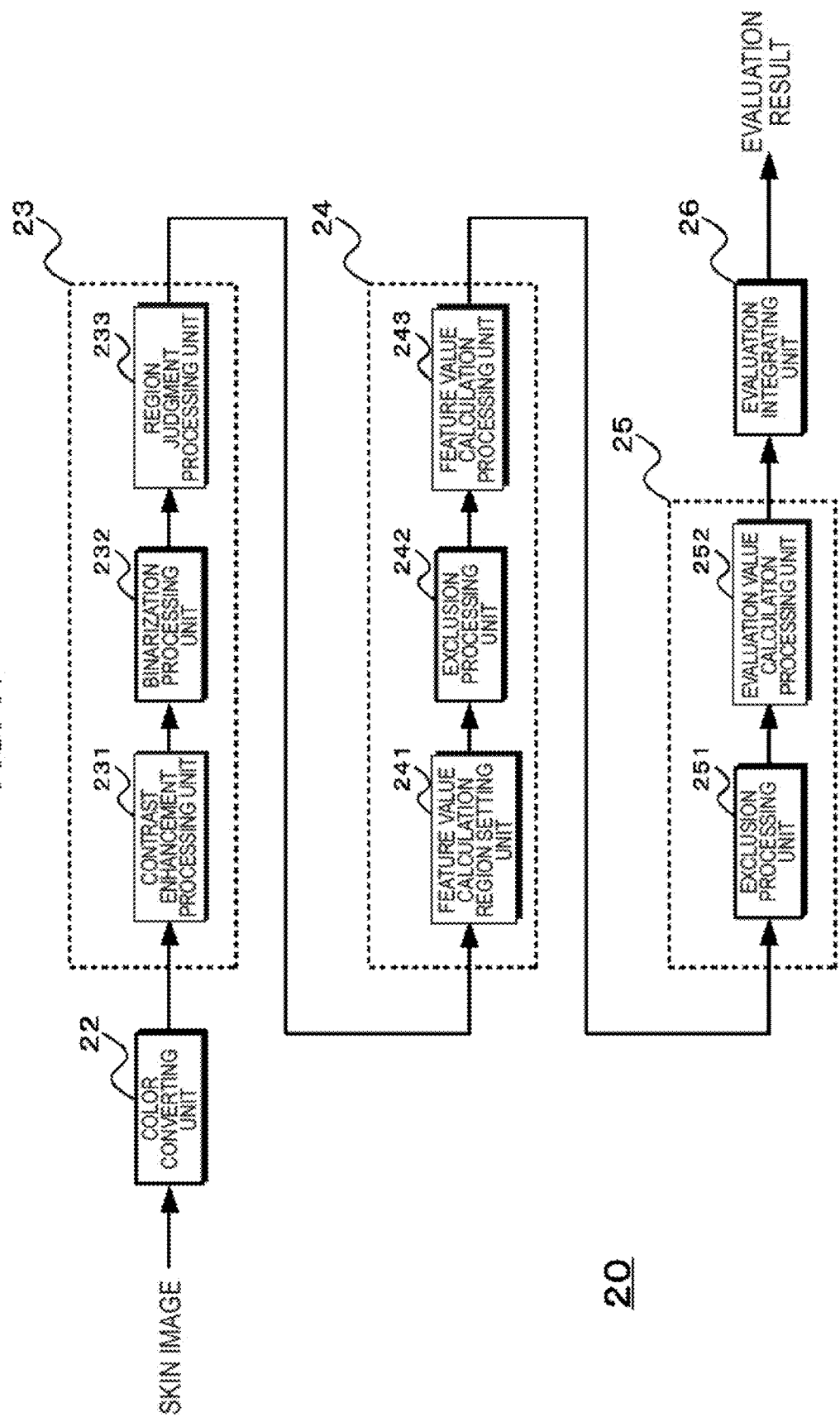
FIG. 11 is a view illustrating the configuration of a second embodiment of an image processing device.

FIG. 11 illustrates the configuration of the second embodiment of an image processing device. An image processing device 20 has a color converting unit 22, a region dividing unit 23, a feature value calculating unit 24, an evaluating unit 25, and an evaluation integrating unit 26. The region dividing unit 23 has a contrast enhancement processing unit 231, a binarization processing unit 232, and a region judgment processing unit 233. The feature value calculating unit 24 has a feature value calculation region setting unit 241, an exclusion processing unit 242, and a feature value calculation processing unit 243. The evaluating unit 25 has an exclusion processing unit 251 and an evaluation value calculation processing unit 252.

The color converting unit 22 converts a color space of a skin image to a desired color space. The color converting unit 22 converts a skin image to a desired color space, for example, an HSV color space which is a color space suitable for skin evaluation. The color converting unit 22 may convert the color space to a L*a*b* color space.

The contrast enhancement processing unit 231 of the region dividing unit 23 can appropriately perform binarization processing by performing contrast enhancement processing. The contrast enhancement processing unit 231 performs the contrast enhancement processing of the S values of the HSV color space, e.g., processing based on a histogram, such as contrast limited adaptive histogram equalization (CLAHE), to generate a contrast enhanced image. The contrast enhancement processing unit 231 may perform gamma correction processing of the S values to generate an image in which the contrast is enhanced. The contrast enhancement processing unit 231 may perform contrast enhancement processing of the L* values of the L*a*b* color space to generate a contrast enhanced image.

The binarization processing unit 232 compares the contrast enhanced image generated by the contrast enhancement processing unit 231 with a predetermined threshold value to generate a binarized image in which a skin image is binarized to a skin region and a non-skin region.

The region judgment processing unit 233 judges that the non-skin region is equivalent to any one of body hair, pores, spots, and the like. The region judgment processing unit 233 performs processing for extracting a structure, for example, morphology processing, in order to facilitate the judgment of the non-skin region in the binarized image. The region judgment processing unit 233 deletes isolated points, connects discontinuous points, and the like by the morphology processing, and then brings the shape of the non-skin regions close to the corresponding subjects (body hair, pores, spots, and the like). Furthermore, the region judgment processing unit 233 judges that the non-skin region is equivalent to any one of body hair, pores, spots, and the like based on the image subjected to the morphology processing and the like. For example, when the shape of the non-skin region is a linear shape, the non-skin region is judged to be a body hair region. When the shape of the non-skin region is a circular shape and the size is within a threshold value range determined beforehand in accordance with the pore size, the non-skin region is judged to be a pore region. When the shape of the non-skin region is a shape different from a linear shape and a circular shape and the size is larger than the predetermined size, the non-skin region is judged to be a spot region. The second embodiment describes a case where a body hair region, a pore region, and a spot region are judged, and then an evaluation value is calculated in each region. However, it may be configured so that a mole region and the like are distinguished based on the shape, size, and the like of the non-skin region, and then evaluation values of these regions may be calculated.

The feature value calculation region setting unit 241 of the feature value calculating unit 24 sets a plurality of feature value calculation regions in each divided region of the skin region and the body hair region, the pore region, and the spot region of the non-skin regions. The feature value calculation region setting unit 241 sets a plurality of feature value calculation regions having a polygonal shape, a circular shape, an oval shape, and the like in each of the skin region and the body hair region, the pore region, and the spot region of the non-skin regions. The feature value calculation regions may be different in the shape or size and may have a portion where the region is overlapped with the other region.

The exclusion processing unit 242 performs processing of excluding greatly different values in each of a group of the H values and a group the V values of the HSV color space in each feature value calculation region. The exclusion processing unit 242 performs a test of rejection of the H values and the V values in each feature value calculation region as described above, and excludes greatly different values.

The feature value calculation processing unit 243 performs statistical processing using the H values and the V values after the exclusion processing of the HSV color space in each feature value calculation region, and then calculates the feature value of the color property. The feature value calculation processing unit 243 calculates an average value, for example, by the statistical processing to give the same as the feature value. As the feature value, the mode, the median value, and the maximum value may be used. When the number of the H values and the V values which represent that reflection is strongly saturated increase, the minimum value may be used.

Thus, the feature value calculation processing unit 243 calculates the feature value using the H values and the V values after the exclusion processing of the HSV color space, and therefore can calculate the feature value which strongly reflects the feature of the feature value calculation region as compared with the case where the feature value is calculated using the H values and the V values which are not subjected to the exclusion processing.

The exclusion processing unit 251 of the evaluating unit 25 performs processing of excluding a value greatly different from the feature value calculated in each feature value calculation region in each divided region of the skin region and the body hair region, the pore region, and the spot region of the non-skin regions. The exclusion processing unit 251 performs a test of rejection of the feature value calculated in each feature value calculation region using the H values and a test of rejection of the feature value calculated in each feature value calculation region using the V values as described above, and then excludes greatly different feature values.

The evaluation value calculation processing unit 252 performs statistical processing using the feature values after the exclusion processing, and then calculates an evaluation value of the color property in each divided region of the skin region and the body hair region, the pore region, and the spot region of the non-skin regions. The evaluation value calculation processing unit 252 performs statistical processing of the H values using the feature values after the exclusion processing, and then calculates an average value, for example, to give the same as the evaluation value. As the evaluation value, the mode and the median value may be used. Similarly, the evaluation value calculation processing unit 252 performs statistical processing of the V values using the feature values after the exclusion processing, and then calculates an average value, for example, to give the same as the evaluation value. As the evaluation value, the mode and the median value may be used.

Thus, the evaluation value calculation processing unit 252 calculates the feature value after the exclusion processing of the HSV color space, and therefore can calculate the feature value which strongly reflects the feature of each divided region as compared with the case where an evaluation value is calculated from the feature values based on the H values and the V values which are not subjected to the exclusion processing.

The evaluation integrating unit 26 integrates the evaluation values calculated for the skin region and the body hair region, the pore region, and the spot region of the non-skin regions to give the same as a skin evaluation value. Moreover, the evaluation integrating unit 26 may weight the evaluation value calculated in each divided region, and then integrate the weighted evaluation values.

[3-2. Operation of Second Embodiment]

Figure 12:
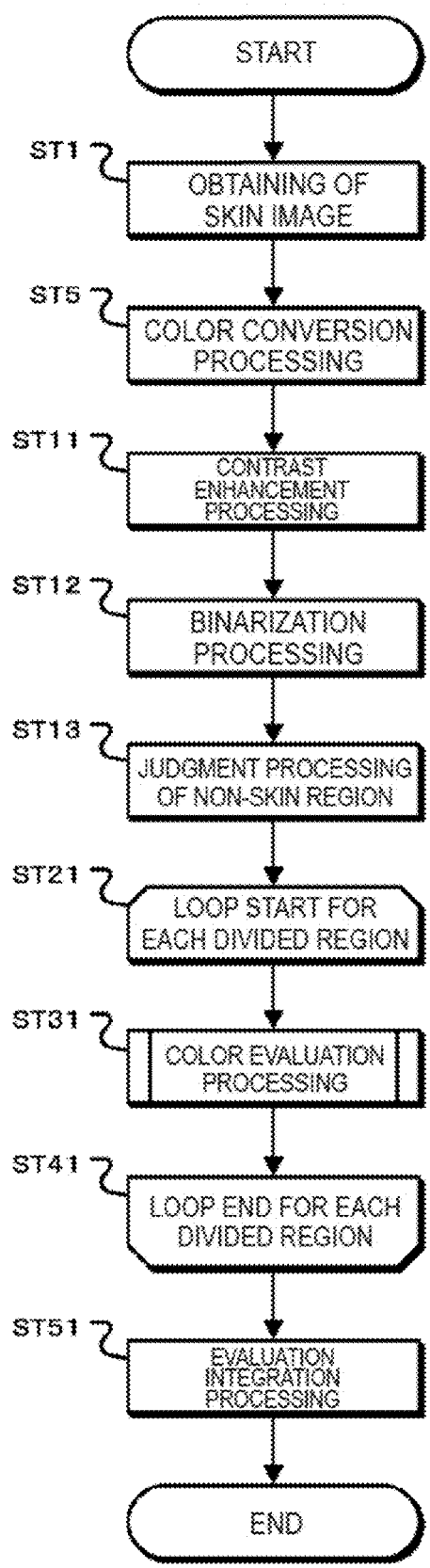
FIG. 12 is a flow chart showing an operation of the second embodiment of the image processing device.

FIG. 12 is a flow chart showing an operation of the second embodiment of the image processing device.

In Step ST1, the image processing device 20 obtains a skin image. The image processing device 20 obtains the skin image generated by the imaging device 11 or the skin image generated by the imaging device 11, and then stored. Then, the process proceeds to Step ST5.

In Step ST5, the image processing device 20 performs color conversion processing of the skin image. The image processing device 20 converts the skin image to an HSV color space (or L*a*b* color space), for example. Then, the process proceeds to Step ST11.

In Step ST11, the image processing device 20 performs contrast enhancement processing. The image processing device 20 performs contrast enhancement processing of an image of the S value suitable for the skin region division in such a manner that appropriate binarization processing can be performed. Then, the process proceeds to Step ST12.

In Step ST12, the image processing device 20 performs binarization processing. The image processing device 20 performs the binarization processing using an image after the contrast enhancement processing, and then divides a skin image into a skin region and non-skin regions. Then, the process proceeds to Step ST13.

In Step ST13, the image processing device 20 performs judgment processing of the non-skin regions. The image processing device 20 judges, for example, non-skin regions equivalent to pores, non-skin regions equivalent to spots, and non-skin regions equivalent to body hair based on the shape and the size of the non-skin regions. Then, the process proceeds to Step ST21.

Step ST21 is a loop start point of each divided region, e.g., the skin region, the pore region, the spot region, and the body hair region.

In Step ST31, the image processing device 20 performs color evaluation. The image processing device 20 performs the color evaluation illustrated in FIG. 7 in each divided region, and then calculates evaluation values. Then, the process proceeds to Step ST41.

Step ST41 is a loop end point of each divided region. More specifically, an evaluation value is calculated for each of a group of the H values and a group of the V values in each divided region by the processing from Step ST21 to Step ST41. Then, the process proceeds to Step ST51.

In Step ST51, the image processing device 20 performs evaluation integration processing. The image processing device 20 integrates the evaluation value calculated in each of the skin regions, the pore regions, the spot regions, and the body hair regions to calculate the skin evaluation value.

Next, the evaluation integration processing of the image processing device 20 is described. The image processing device 20 performs the same processing as that of the first embodiment in each divided region, and then integrates the evaluation value calculated in each divided region to calculate the skin evaluation value. Expressions (1) and (2) show a case where the evaluation value calculated in each divided region is weighted, and then integrated as an example.

Skin color tone evaluation value $$=a1\times(\text{Evaluation value of } H \text{ values of skin region})$$
$$+b1\times(\text{Evaluation value of } H \text{ values of pore regions})$$
$$+c1\times(\text{Evaluation value of } H \text{ values of spot regions})$$
$$+d1\times(\text{Evaluation value of } H \text{ values of body hair regions}) \quad (1)$$

Skin brightness evaluation value $$=a2\times(\text{Evaluation value of } V \text{ values of skin region})$$
$$+b2\times(\text{Evaluation value of } V \text{ values of pore regions})$$
$$+c2\times(\text{Evaluation value of } V \text{ values of spot regions})$$
$$+d2\times(\text{Evaluation value of } V \text{ values of body hair regions}) \quad (2)$$

In Expressions (1) and (2), "a1, b1, c1, d1, a2, b2, c2, and d2" are the weighting parameters. These parameters may be set according to the size of the regions and the parameters set beforehand so that the optimal evaluation result is obtained using a plurality of samples may be used.

By changing the parameters, the evaluation value of a desired region and the evaluation value of a region excluding a desired region can be calculated. For example, when "a1=b1=c1=a2=b2=c2=0" is set, the evaluation value of the body hair regions can be obtained. When "b1=d1=b2=d2=0" is set, the evaluation value of the skin excluding the body hair regions and the pore regions can be obtained.

The second embodiment above describes the case where the pore regions, the spot regions, and body hair regions in the non-skin region are divided but a skin region may be divided into regions based on each component. For example, the skin region is divided into a cristae cutis region and a sulci cutis region, an evaluation value for each region is calculated as described above, and then the evaluation values are integrated. When such region division is performed, in the case where the V values of the cristae cutis region and the H values and the V values of the cristae cutis region are set as indices indicating the skin transparency, for example, the skin transparency can also be evaluated by the use of the evaluation value of the cristae cutis region.

As described above, in the second embodiment, a skin region, pore regions, spot regions, and the like are divided from a skin image, color evaluation is performed in each divided region, and then color evaluation in each divided region is integrated. Therefore, according to the second embodiment, the color can be evaluated for each of the skin region, the pore regions, the spot regions, and the like. Moreover, according to the second embodiment, the color of the entire skin including the pore regions, the spot regions, and the like can be evaluated with good accuracy. Also in the second embodiment, the exclusion processing of excluding greatly different values is performed, and then evaluation values are calculated, and therefore an evaluation value which strongly reflects the feature of each region can be calculated.

4. Third Embodiment

Next, a third embodiment describes a case where a skin image is divided into regions in the depth direction, and then an evaluation result of each region is integrated to evaluate the skin.

Figure 13:
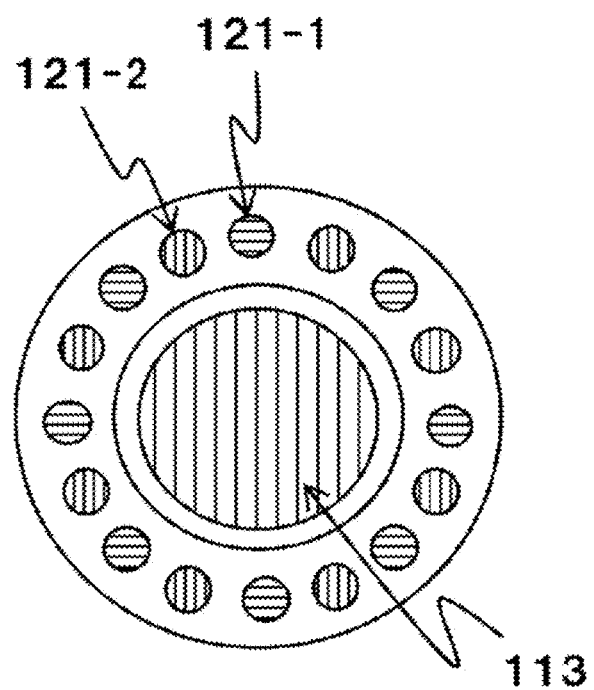
FIG. 13 is a view illustrating a light source as an attachment.
Figure 14:
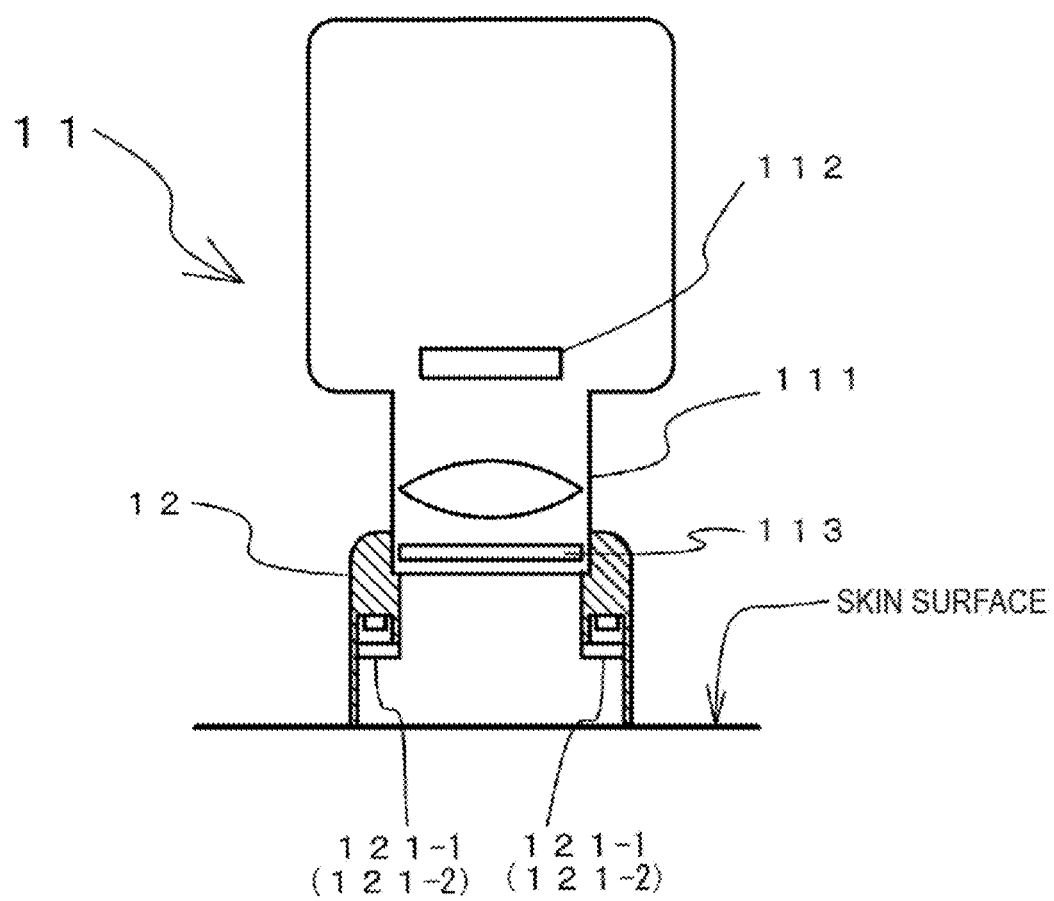
FIG. 14 is a view illustrating the position of the imaging device in imaging.

In this case, as illustrated in FIG. 13, the attachment 12 is provided with white LEDs 121-1 provided with a polarizing filter of a predetermined polarization plane and white LEDs 121-2 provided with a polarizing filter in which the polarization plane, for example, is orthogonal to the predetermined polarization plane as a light source. The imaging device 11 provided with the attachment 12 is provided with a polarizing filter 113 in which a polarization plane is orthogonal to a predetermined polarization plane on an optical path to the imaging unit 112 as illustrated in FIG. 14, for example. By providing the polarizing filter as described above, when an image is captured by turning on the whites LEDs 121-1, skin surface reflection components are cut, and then an image of internal reflection components can be obtained and when an image is captured by turning on the white LEDs 121-2, an image of the skin surface can be obtained. For the lighting of skin, another configuration may be employed insofar as captured images different in the polarization plane are obtained.

In the imaging device 11, a microlens array in which a plurality of microlenses constituted by a liquid lens, a liquid crystal lens, and the like are arranged in the shape of a matrix is used as an imaging lens similarly as in JP 2008-262336A. In this case, skin images different in the depth direction may be generated by controlling a voltage to be applied to the microlens to change the focal position. Furthermore, a so-called light field camera capable of obtaining, in addition to an intensity distribution of light on a light receiving surface of an imaging device, traveling direction information of the light using a microlens array constituted by a plurality of microlenses may be used as the imaging device 11. In this case, a skin image is reconstructed in which the focal position is set at an arbitrary position in the depth direction from the intensity distribution and the traveling direction information of the light.

[4-1. Configuration of Third Embodiment]

Figure 15:
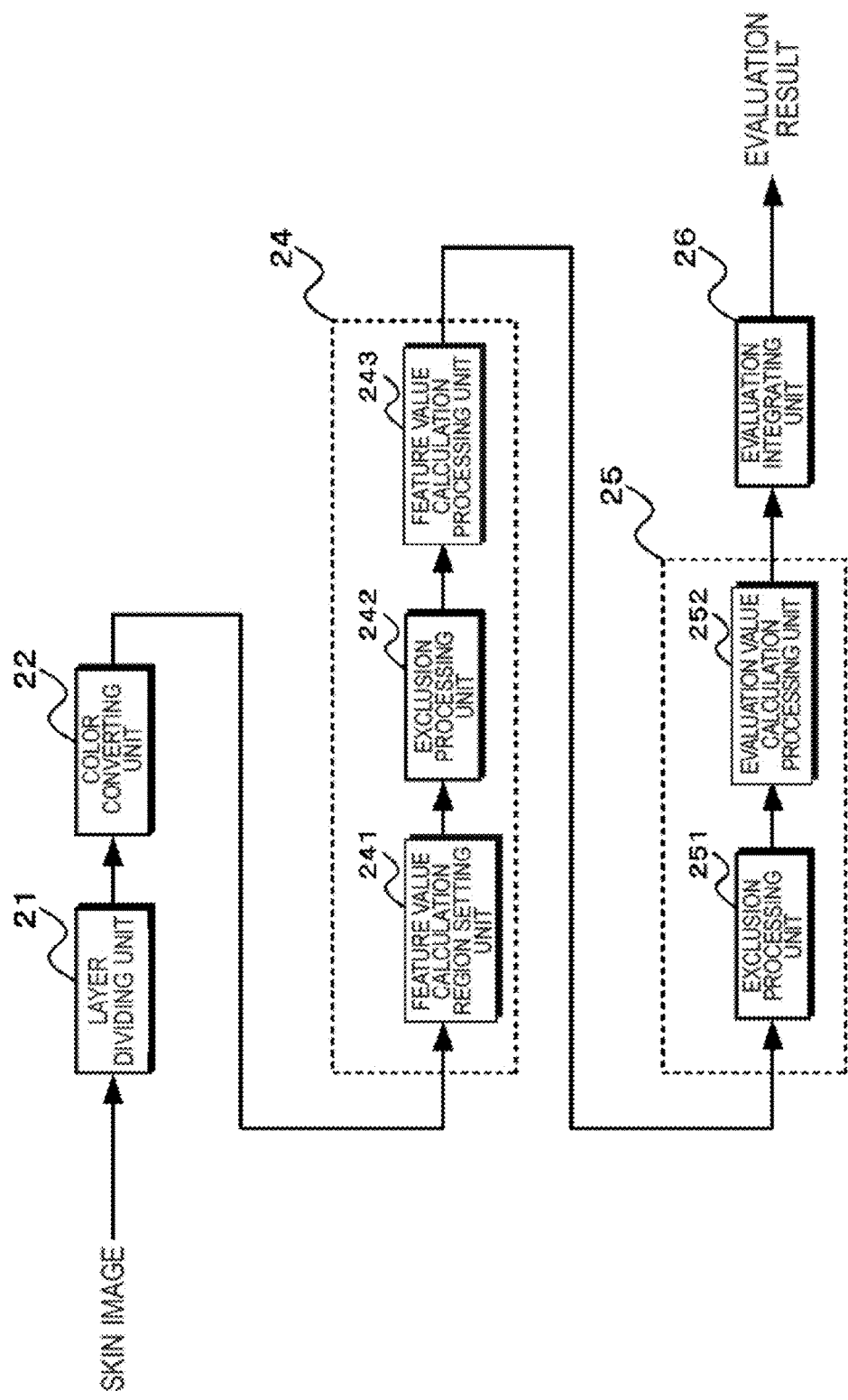
FIG. 15 is a view illustrating the configuration of a third embodiment of an image processing device.

FIG. 15 illustrates the configuration of a third embodiment of an image processing device. An image processing device 20 has a layer dividing unit 21, a color converting unit 22, a feature value calculating unit 24, an evaluating unit 25, and an evaluation integrating unit 26. The feature value calculating unit 24 has a feature value calculation region setting unit 241, an exclusion processing unit 242, and a feature value calculation processing unit 243. The evaluating unit 25 has an exclusion processing unit 251 and an evaluation value calculation processing unit 252.

The layer dividing unit 21 obtains a plurality of skin images different in the depth direction. The layer dividing unit 21 obtains an image of the skin surface and an image showing the inside of skin, for example. In the following description, the images different in the depth direction are referred to as images different in the layer. As the image showing the inside of skin, a polarizing filter is provided on the front of a light source and an imaging unit, so that the polarization planes are orthogonal to each other as described above, whereby skin surface reflection components are cut and an image of reflection components of the inside of skin is generated. Moreover, skin images different in the depth direction may be generated by controlling a voltage to be applied to the microlens to change the focal position. Furthermore, when a light field camera is used, the layer dividing unit 21 may reconstruct a skin image in which the focal position is set at an arbitrary position in the depth direction from an intensity distribution and traveling direction information of light.

The color converting unit 22 converts a color space of a skin image to a desired color space. The color converting unit 22 converts a skin image to a desired color space, for example, an HSV color space which is a color space suitable for skin evaluation. The color converting unit 22 may convert a skin image to a L*a*b* color space.

The feature value calculation region setting unit 241 of the feature value calculating unit 24 sets a plurality of feature value calculation regions in a plurality of skin images different in the depth direction. The feature value calculation region setting unit 241 sets a plurality of feature value calculation regions having a polygonal shape a circular shape, an oval shape, and the like in the skin image of each layer. The feature value calculation regions may be different in the shape or size, and may have a portion where the region is overlapped with the other region.

The exclusion processing unit 242 performs processing of excluding greatly different values in each of a group of the H values and a group of the V values of the HSV color space in each feature value calculation region. The exclusion processing unit 242 performs a test of rejection of the H value and the V value in each feature value calculation region as described above, and excludes greatly different values.

The feature value calculation processing unit 243 performs statistical processing using the H values and the V values after the exclusion processing of the HSV color space in each feature value calculation region, and then calculates the feature value of the color property. The feature value calculation processing unit 243 calculates an average value, for example, by the statistical processing to give the same as the feature value. As the feature value, the mode, the median value, and the maximum value may be used.

Thus, the feature value calculation processing unit 243 calculates the feature values using the H values and the V values after the exclusion processing of the HSV color space, and therefore can calculate the feature value which strongly reflects the feature of the feature value calculation region as compared with the case where the feature value is calculated using the H values and the V values which are not subjected to the exclusion processing.

The exclusion processing unit 251 of the evaluating unit 25 performs processing of excluding a value greatly different from the feature value calculated in each feature value calculation region in the skin image of each layer. The exclusion processing unit 251 performs a test of rejection of the feature value calculated in each feature value calculation region using the H values and a test of rejection of the feature value calculated in each feature value calculation region using the V values as described above, and then excludes greatly different feature values.

The evaluation value calculation processing unit 252 performs statistical processing using the feature values after the exclusion processing, and then calculates an evaluation value of the color property in the skin image of each layer. The evaluation value calculation processing unit 252 performs statistical processing of the H values using the feature values after the exclusion processing, and then calculates an average value, for example, to give the same as the evaluation value. As the evaluation value, the mode and the median value may be used. Similarly, the evaluation value calculation processing unit 252 performs statistical processing of the V values using the feature values after the exclusion processing, and then calculates an average value, for example, to give the same as the evaluation value. As the evaluation value, the mode and the median value may be used.

Thus, the evaluation value calculation processing unit 252 calculates the feature values after the exclusion processing of the HSV color space, and therefore can calculate the feature value which strongly reflects the feature of each divided region as compared with the case where an evaluation value is calculated from the feature values based on the H values and the V values which are not subjected to the exclusion processing.

The evaluation integrating unit 26 integrates the evaluation values calculated for the skin image of each layer to give the same as a skin evaluation value. Moreover, the evaluation integrating unit 26 may weight the evaluation value calculated in each layer, and then integrate the weighted evaluation values.

[4-2. Operation of Third Embodiment]

Figure 16:
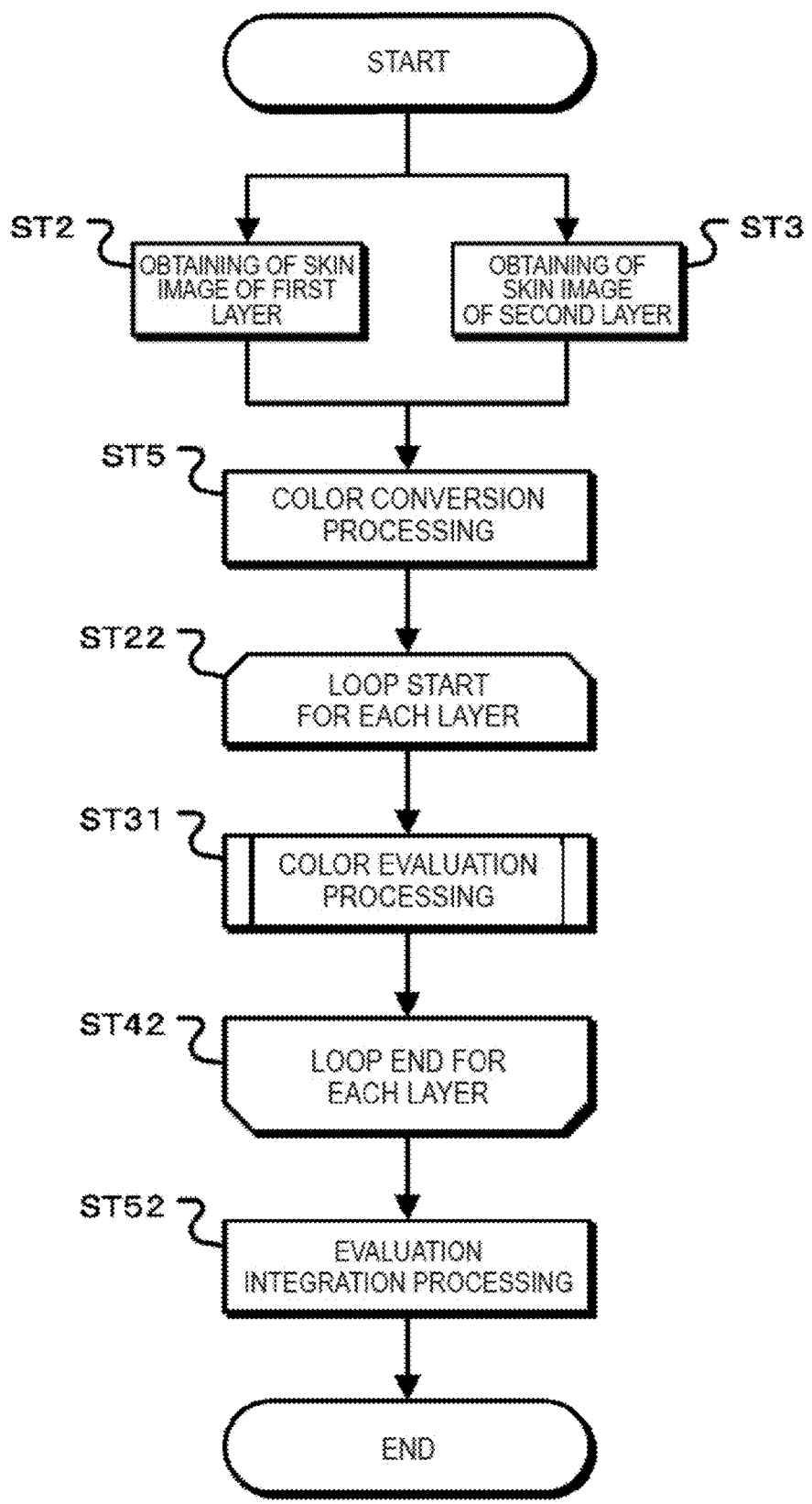
FIG. 16 is a flow chart showing an operation of the third embodiment of the image processing device.

FIG. 16 is a flow chart showing an operation of a third embodiment of an image processing device.

In Step ST2, the image processing device 20 obtains a skin image of a first layer. The image processing device 20 obtains the first layer, e.g., an image of the skin surface generated by the imaging device 11 or an image of the skin surface generated by the imaging device 11, and then stored. Then, the process proceeds to Step ST5.

In Step ST3, the image processing device 20 obtains a skin image of a second layer. The image processing device 20 obtains a second layer, e.g., an image of the inside of skin generated by the imaging device 11 or an image of the inside of skin generated by the imaging device 11, and then stored. Then, the process proceeds to Step ST5.

In Step ST5, the image processing device 20 performs color conversion processing of the skin image. The image processing device 20 converts the skin image to an HSV color space (or L*a*b* color space), for example. Then, the process proceeds to Step ST22. Step 22 is a loop start point of each layer.

In Step ST31, the image processing device 20 performs color evaluation. The image processing device 20 performs color evaluation illustrated in FIG. 7 in each divided region, and then calculates an evaluation value. Then, the process proceeds to Step ST42.

Step ST42 is a loop end point of each layer. More specifically, an evaluation value is calculated for each of a group of the H values and a group of the V values in each layer by the processing from Step ST22 to Step ST42. Then, the process proceeds to Step ST52.

In Step ST52, the image processing device 20 performs evaluation integration processing. The image processing device 20 integrates the evaluation value calculated in the skin image of each layer to calculate the skin evaluation value.

FIG. 17 illustrates an example of the skin image. FIG. 17(A) shows the skin surface and FIG. 17 (B) shows the inside of skin. The evaluation integration processing of the image processing device 20 is described. The image processing device 20 integrates the evaluation value calculated in each layer to calculate the skin evaluation value. Expressions (3) and (4) show a case of weighting the evaluation value calculated in each layer and then integrating the weighted values as an example.

Skin color tone evaluation value

=$e41$×(Evaluation value of $H$ values of skin surface)

+$f1$×(Evaluation value of $H$ values of inside of skin)  (3)

Skin brightness evaluation value

=$e2$×(Evaluation value of $V$ values of skin surface)

+$f2$×(Evaluation value of $V$ values of inside of skin)  (4)

In Expressions (3) and (4), "e1, f1, e2, and f2" are the weighting parameters. These parameters may be set according to the size of the regions and the parameters set beforehand so that the optimal evaluation result is obtained using a plurality of samples may be used.

As described above, in the third embodiment, the evaluation is stepwisely performed in the depth direction. Herein, potential spots, dullness, and melanin which can be observed in the image of the inside of skin are also pigment components which determine the skin color. Moreover, the skin color state of the inside of skin comes to the surface by the skin turnover in the near future. Therefore, according to the third embodiment, the evaluation result of the color in the depth direction can be obtained, and therefore a future skin state can be evaluated at early timing, so that skin troubles can be prevented beforehand.

5. Fourth Embodiment

Next, a fourth embodiment describes a case where a skin image is divided into regions in the planar direction and in the depth direction, and then the evaluation result of each region is integrated to evaluate the skin.

[5-1. Configuration of Fourth Embodiment]

Figure 18:
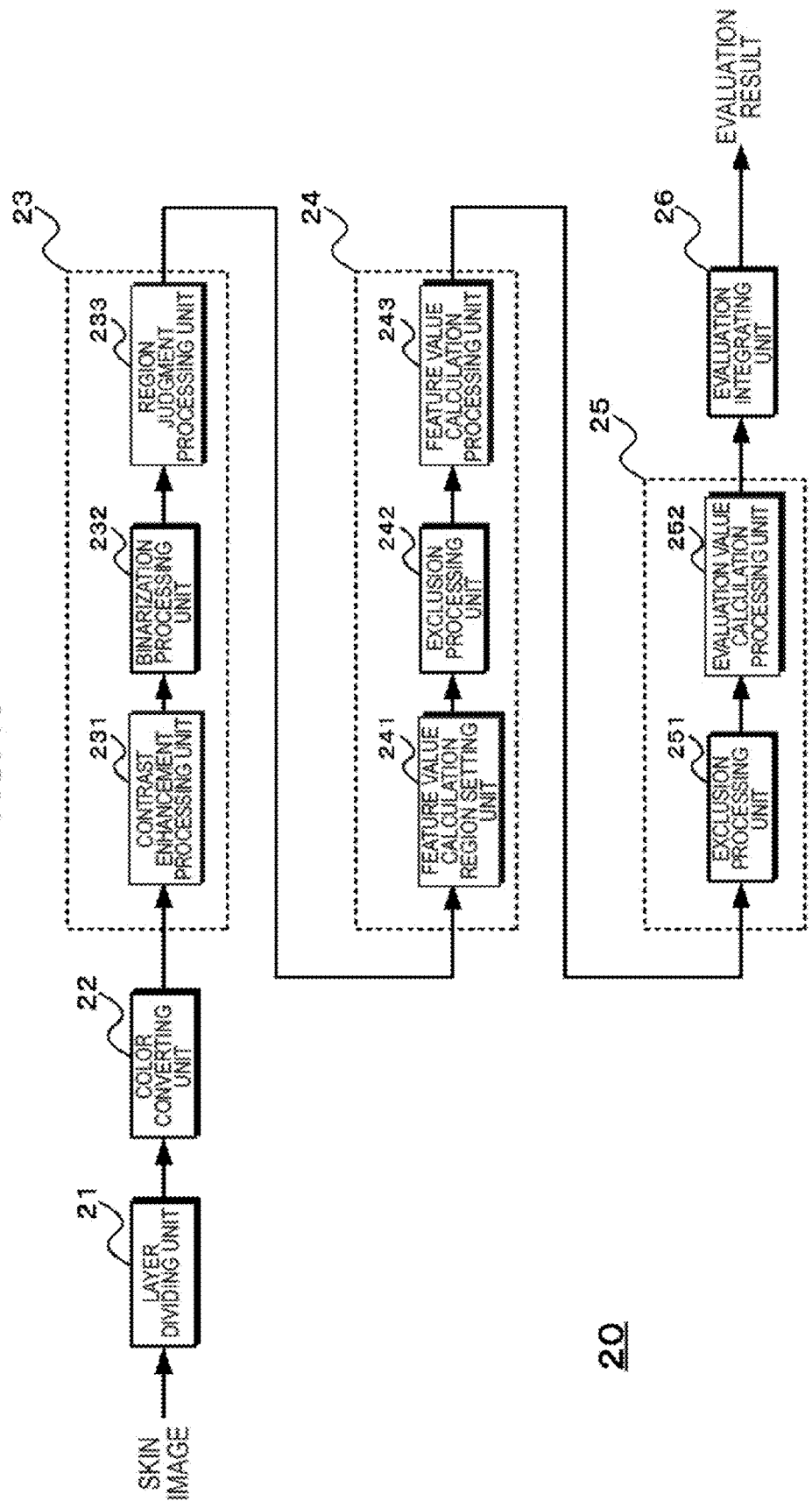
FIG. 18 is a view illustrating the configuration of a fourth embodiment of an image processing device.

FIG. 18 illustrates the configuration of the fourth embodiment of an image processing device. An image processing device 20 has a layer dividing unit 21, a color converting unit 22, a region dividing unit 23, a feature value calculating unit 24, an evaluating unit 25, and an evaluation integrating unit 26. The region dividing unit 23 has a contrast enhancement processing unit 231, a binarization processing unit 232, and a region judgment processing unit 233. The feature value calculating unit 24 has a feature value calculation region setting unit 241, an exclusion processing unit 242, and a feature value calculation processing unit 243. The evaluating unit 25 has an exclusion processing unit 251 and an evaluation value calculation processing unit 252.

The layer dividing unit 21 obtains a plurality of skin images different in the depth direction. The layer dividing unit 21 obtains images of a plurality of layers different in the depth direction, for example, an image showing the skin surface and an image showing the inside of skin similarly as in the third embodiment. More specifically, the layer dividing unit 21 generates an image of reflection components of the inside of skin by cutting skin surface reflection components by providing a polarizing filter on the front of a light source and an imaging unit, so that the polarization planes are orthogonal to each other as described above. Moreover, skin images different in the depth direction may be generated by controlling a voltage to be applied to the microlens to change the focal position. Furthermore, when a light field camera is used, the layer dividing unit 21 may reconstruct a skin image in which the focal position is set at an arbitrary position in the depth direction from an intensity distribution and traveling direction information of light.

The color converting unit 22 converts a color space of a skin image to a desired color space. The color converting unit 22 converts a skin image to a desired color space, for example, an HSV color space which is a color space suitable for skin evaluation. The color converting unit 22 may convert a skin image to a L*a*b* color space.

The contrast enhancement processing unit 231 of the region dividing unit 23 can appropriately perform binarization processing by performing contrast enhancement processing. The contrast enhancement processing unit 231 performs the contrast enhancement processing of the S values of the HSV color space, e.g., processing based on a histogram, such as contrast limited adaptive histogram equalization (CLAHE), to generate a contrast enhanced image. The contrast enhancement processing unit 231 may perform gamma correction of the S values to generate an image in which the contrast is enhanced. The contrast enhancement processing unit 231 may perform contrast enhancement processing of the L* values of the L*a*b* color space to generate a contrast enhanced image.

The binarization processing unit 232 compares the contrast enhanced image generated by the contrast enhancement processing unit 231 with a predetermined threshold value to generate a binarized image in which a skin image is binarized to a skin region and a non-skin region.

The region judgment processing unit 233 judges that the non-skin region is equivalent to any one of body hair, pores, spots, and the like. The region judgment processing unit 233 performs processing for extracting a structure, for example, morphology processing, in order to facilitate the judgment of the non-skin region in the binarized image. The region judgment processing unit 233 judges that the non-skin region is equivalent to any one of body hair, pores, spots, and the like based on the image subjected to the morphology processing. For example, when the shape of the non-skin region is a linear shape, the non-skin region is judged to be a body hair region. When the shape of the non-skin region is a circular shape and the size is within a threshold value range determined beforehand in accordance with the pore size, the non-skin region is judged to be a pore region. When the shape of the non-skin region is a shape different from a linear shape and a circular shape and the size is larger than a predetermined size, the non-skin region is judged to be a spot region. Also in the fourth embodiment, it may be configured so that a mole region and the like are distinguished based on the shape, size, and the like of the non-skin region, and then evaluation values of these regions are calculated in the same manner as in the second embodiment. In the fourth embodiment, when the skin image shows the inside of skin, the judgment of a body hair region may be excluded. When the skin image shows the skin surface, a cristae cutis region and a sulci cutis region may be judged in the skin region.

The feature value calculation region setting unit 241 of the feature value calculating unit 24 sets a plurality of feature value calculation regions in each layer and each divided region of the skin region and the body hair region, the pore region, and the spot region of the non-skin regions. The feature value calculation region setting unit 241 sets a plurality of feature value calculation regions having a polygonal shape, a circular shape, an oval shape, and the like in each layer and each of the skin region and the body hair region, the pore region, and the spot region of the non-skin regions. The feature value calculation regions may be different in the shape or size and may have a portion where the region is overlapped with the other region.

The exclusion processing unit 242 performs processing of excluding greatly different values in each of a group of the H values and a group of the V values of the HSV color space in each feature value calculation region. The exclusion processing unit 242 performs a test of rejection of the H values and the V values in each feature value calculation region as described above, and excludes greatly different values.

The feature value calculation processing unit 243 performs statistical processing using the H values and the V values after the exclusion processing of the HSV color space in each feature value calculation region, and then calculates the feature value of the color property. The feature value calculation processing unit 243 calculates an average value, for example, by the statistical processing to give the same as the feature value. As the feature value, the mode, the median value, and the maximum value may be used.

Thus, the feature value calculation processing unit 243 calculates the feature values using the H values and the V values after the exclusion processing of the HSV color space. Therefore, the feature value is a value which strongly reflects the feature of the feature value calculation region as compared with the case where the feature value is calculated using the H values and the V values which are not subjected to the exclusion processing.

The exclusion processing unit 251 of the evaluating unit 25 performs processing of excluding a value greatly different from the feature value calculated in each feature value calculation region in each layer and each divided region of the skin region and the body hair region, the pore region, and the spot region of the non-skin regions. The exclusion processing unit 251 performs a test of rejection of the feature value calculated in each feature value calculation region using the H values and a test of rejection of the feature value calculated in each feature value calculation region using the V values as described above, and then excludes greatly different feature values.

The evaluation value calculation processing unit 252 performs statistical processing using the feature value after the exclusion processing, and then calculates an evaluation value of the color property in each layer and each divided region of the skin region and the body hair region, the pore region, and the spot region of the non-skin regions. The evaluation value calculation processing unit 252 performs statistical processing of the H values using the feature values after the exclusion processing, and then calculates an average value, for example, to give the same as the evaluation value. As the evaluation value, the mode and the median value may be used. Similarly, the evaluation value calculation processing unit 252 performs statistical processing of the V values using the feature values after the exclusion processing, and then calculates an average value, for example, to give the same as the evaluation value. As the evaluation value, the mode and the median value may be used.

Thus, the evaluation value calculation processing unit 252 calculates the feature values after the exclusion processing of the HSV color space. Therefore, the feature value is a value which strongly reflects the feature of the divided regions as compared with the case where evaluation values are calculated from the feature values based on the H values and the V values which are not subjected to the exclusion processing.

The evaluation integrating unit 26 integrates the evaluation value calculated in each divided region, e.g., each layer and the skin region and each of the body hair region, the pore region, and the spot region of the non-skin regions to give the same as a skin evaluation value. Moreover, the evaluation integrating unit 26 may weight the evaluation value calculated in each layer, and then integrate the weighted evaluation values.

[5-2. Operation of Fourth Embodiment]

Figure 19:
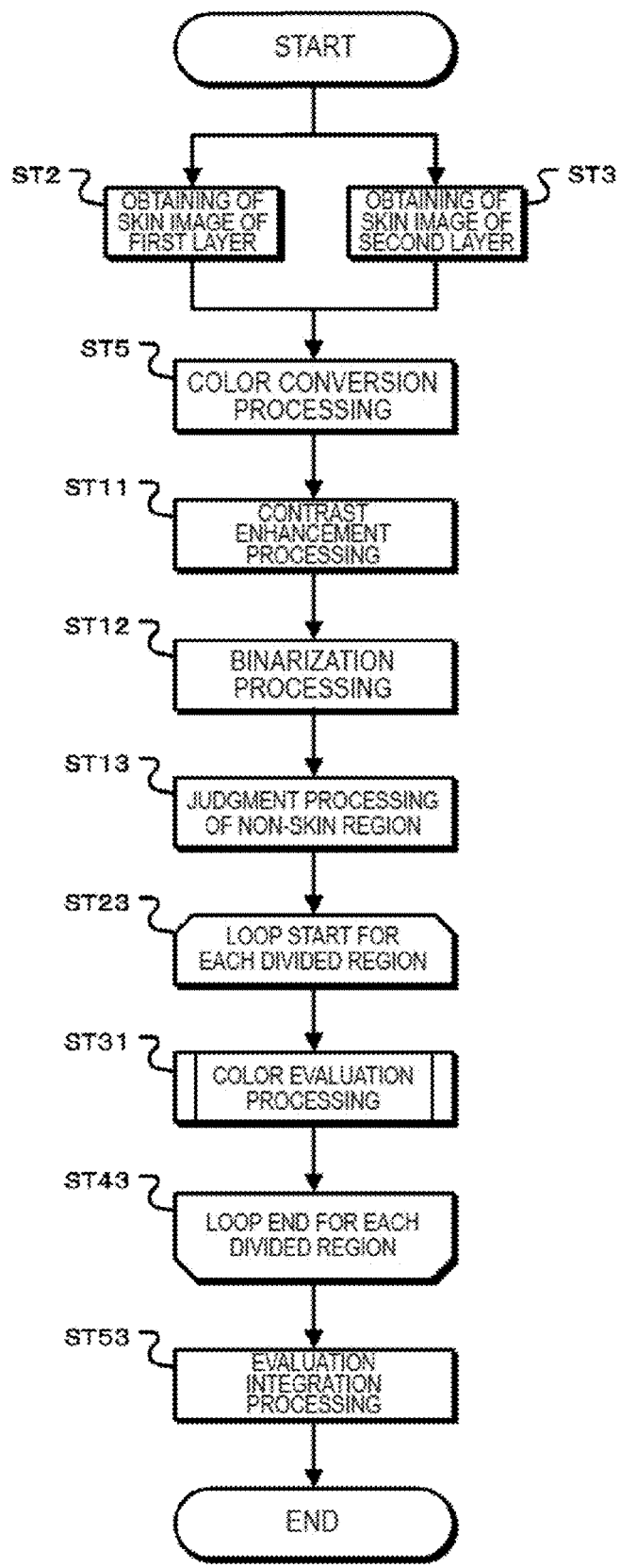
FIG. 19 is a flow chart showing an operation of the fourth embodiment of the image processing device.

FIG. 19 is a flow chart showing an operation of the fourth embodiment of the image processing device.

In Step ST2, the image processing device 20 obtains a skin image of a first layer. The image processing device 20 obtains the first layer, e.g., an image of the skin surface generated by the imaging device 11 or an image of the skin surface generated by the imaging device 11, and then stored. Then, the process proceeds to Step ST5.

In Step ST3, the image processing device 20 obtains a skin image of a second layer. The image processing device 20 obtains the second layer, e.g., an image of the inside of skin generated by the imaging device 11 or a skin image of the inside of skin generated by the imaging device 11, and then stored. Then, the process proceeds to Step ST5.

In Step ST5, the image processing device 20 performs color conversion processing of the skin image. The image processing device 20 converts the skin image to an HSV color space (or L*a*b* color space), for example. Then, the process proceeds to Step ST11.

In Step ST11, the image processing device 20 performs contrast enhancement processing. The image processing device 20 performs contrast enhancement processing of an image of the S values suitable for the skin region division in such a manner that appropriate binarization processing can be performed. Then, the process proceeds to Step ST12.

In Step ST12, the image processing device 20 performs binarization processing. The image processing device 20 performs the binarization processing using an image after the contrast enhancement processing, and then divides a skin image into a skin region and non-skin regions. Then, the process proceeds to Step ST13.

In Step ST13, the image processing device 20 performs judgment of the non-skin regions. The image processing device 20 judges, for example, non-skin regions equivalent to pores, non-skin regions equivalent to spots, and non-skin regions equivalent to body hair based on the shape and the size of the non-skin regions. Then, the process proceeds to Step ST23.

Step ST23 is a loop start point of each divided region, e.g., each layer and the skin region, the pore region, the spot region, and the body hair region.

In Step ST31, the image processing device 20 performs color evaluation. The image processing device 20 performs the color evaluation illustrated in FIG. 7 in each divided region, and then calculates evaluation values. Then, the process proceeds to Step ST43.

Step ST43 is a loop end point of each divided region. More specifically, an evaluation value is calculated for each of a group of the H values and a group of the V values in each layer and each of the skin region, the pore region, the spot region, and the body hair region by the processing from Step ST23 to Step ST43. Then, the process proceeds to Step ST53.

In Step ST53, the image processing device 20 performs evaluation integration. The image processing device 20 integrates the evaluation value calculated for the skin image of each layer to calculate the skin evaluation value.

In the evaluation integration, the evaluation value of the skin color tone may be calculated using Expressions (1) and (3) and the evaluation value of the skin brightness may be calculated using Expressions (2) and (4).

As described above, in the fourth embodiment, division in the planar direction and in the depth direction is performed, an evaluation value is calculated in each divided region, and then the evaluation values are integrated. Therefore, the color of each of the skin region, the pore region, the spot region, and the like and the color of the entire skin including the pore region, the spot region, and the like can be more highly evaluated. According to the fourth embodiment, advice and the like for preventing skin troubles beforehand can be given based on the evaluation result.

Incidentally, the processing described in the present specification can be executed by hardware, software, or a combination of both. The software can execute the processing by installing a program recording a processing sequence into a memory in a computer integrated with dedicated hardware, or by installing the program in a general purpose computer executable of various kinds of processing.

For example, the program can previously be recorded in a hard disk drive, ROM (Read Only Memory) or the like as a recording medium. Or the program can temporarily or permanently be stored (recorded) in a removable medium such as a flexible disk, CD-ROM (Compact Disc Read Only Memory), MO (Magneto optical) disk, DVD (Digital Versatile Disc), magnetic disk, or semiconductor memory card. Such a removable recording medium can be provided as so-called packaged software.

Moreover, the program not only be installed in the computer form the removable recording medium but also may be installed by wireless or wired transferring into the computer via a network such as a LAN (Local Area Network) and the Internet from download sites. The computer can undergo installation of the received program, which is transferred like that, into the recording medium such as the mounted hard disk drive.

It should be understood by those skilled in the art that various modifications, combinations, sub-combinations, and alterations may occur depending on design requirements and other factors insofar as they are within the scope of the appended claims or the equivalents thereof.

Additionally, the image processing device of the present technology may also be configured as below.

(1) An image processing device including:
 a dividing unit which divides a captured image of skin into regions in a multidimensional manner;
 a feature value calculating unit which calculates a feature value of a color property in each region divided by the dividing unit; and
 an evaluating unit which calculates an evaluation value of the skin using the feature values calculated by the feature value calculating unit.

(2) The image processing device according to (1),
 wherein the dividing unit performs the division in at least one of a planar direction and a depth direction.

(3) The image processing device according to (1) or (2),
 wherein the dividing unit divides the captured image of the skin into a skin region and a non-skin region.

(4) The image processing device according to (3),
 wherein the dividing unit divides, as the non-skin region, at least one of a pore region, a spot region, and a body hair region.

(5) The image processing device according to (3) or (4),
 wherein the dividing unit divides the skin region based on each component of the skin.

(6) The image processing device according to any one of (1) to (5),
 wherein the color property is at least any one of skin brightness and skin transparency.

(7) The image processing device according to any one of (1) to (6),
 wherein the evaluating unit weights the feature value calculated in each region, and then calculates an evaluation value of the skin using the weighted feature values.

(8) The image processing device according to any one of (1) to (7),
 wherein the feature value calculating unit and the evaluating unit perform exclusion processing of excluding a greatly different value, and then calculate the feature value and the evaluation value.

(9) The image processing device according to any one of (2) to (8),
 wherein the dividing unit obtains captured images at different positions in the depth direction generated while controlling a polarization plane of a light source and an imaging unit which generates the captured images, obtains captured images at different positions in the depth direction generated while controlling a focal length of the imaging unit, or generates captured images at different positions in the depth direction from an intensity distribution and traveling direction information of light to thereby preform the division of the regions in the depth direction.

According to the image processing device, the image processing method, the program, and the image processing system of the present technology, a skin image is divided into regions in a multidimensional manner, a feature value of a color property is calculated in each divided region, and then a skin evaluation value is calculated using the calculated feature values. Therefore, the skin color can be evaluated with good accuracy as compared with the case where the skin color is evaluated in the entire skin image. Accordingly, the present technology is suitable for electronic devices having a skin imaging function, e.g., digital cameras and mobile terminal devices, and information processing devices which provide various services through a network and the like, for example.

REFERENCE SINGS LIST 10 image processing system
11 imaging device
12 attachment
15, 16 information processing device
20 image processing device
21 layer dividing unit
22 color converting unit
23 region dividing unit
24 feature value calculating unit
25 evaluating unit
26 evaluation integrating unit
50 presentation unit
111 camera cone
112 imaging unit
113 polarizing filter
121 light source
231 contrast enhancement processing unit
232 binarization processing unit
233 region judgment processing unit
241 feature value calculation region setting unit
242, 251 exclusion processing unit
243 feature value calculation processing unit
252 evaluation value calculation processing unit

The invention claimed is:

1. An image processing device comprising:
a dividing unit which divides a captured image of skin into regions in a multidimensional manner;
a feature value calculating unit which calculates a feature value of a color property in each region divided by the dividing unit; and
an evaluating unit which calculates an evaluation value of the skin using the feature values calculated by the feature value calculating unit,
wherein the dividing unit performs division in at least one of a planar direction and a depth direction, and
wherein, when performing division in the depth direction, the dividing unit obtains captured images at different positions in the depth direction generated while controlling a polarization plane of a light source and an imaging unit which generates the captured images, obtains captured images at different positions in the depth direction generated while controlling a focal length of the imaging unit, or generates captured images at different positions in the depth direction from an intensity distribution and traveling direction information of light to thereby preform the division of the regions in the depth direction.

* * * * *